US010520409B2

(12) United States Patent
Erdmann et al.

(10) Patent No.: US 10,520,409 B2
(45) Date of Patent: Dec. 31, 2019

(54) METHOD OF CONTINUOUSLY MEASURING THE SHEAR VISCOSITY OF A PRODUCT PASTE

(71) Applicant: SOCIÉTÉ DES PRODUITS NESTLÉ S.A., Vevey (CH)

(72) Inventors: Peter Erdmann, Bern (CH); Peter Fankhauser, Konolfingen (CH); Nina Laubacher, Gumlingen (CH); Martin Nydegger, Konolfingen (CH); Dale Richard Sanders, Courgevaux (CH); Christian Schmied; Michael Stranzinger, Munsingen (CH); Gerhard Walthert, Aeschlen (CH)

(73) Assignee: Societe des Produits Nestle S.A., Vevey (CH)

( * ) Notice: Subject to any disclaimer, the term of this patent is extended or adjusted under 35 U.S.C. 154(b) by 228 days.

(21) Appl. No.: 15/540,483

(22) PCT Filed: Dec. 22, 2015

(86) PCT No.: PCT/EP2015/081096
§ 371 (c)(1),
(2) Date: Jun. 28, 2017

(87) PCT Pub. No.: WO2016/107803
PCT Pub. Date: Jul. 7, 2016

(65) Prior Publication Data
US 2018/0003606 A1    Jan. 4, 2018

(30) Foreign Application Priority Data

Dec. 31, 2014 (EP) .................................. 14200752

(51) Int. Cl.
*G01N 11/08* (2006.01)
*B01D 1/18* (2006.01)
*B01J 37/00* (2006.01)

(52) U.S. Cl.
CPC ................ *G01N 11/08* (2013.01); *B01D 1/18* (2013.01); *B01J 37/0045* (2013.01)

(58) Field of Classification Search
CPC ........ G01N 11/08; G01N 11/04; G01N 11/06; G01N 1/08; B01D 1/18; B01D 1/20; B01J 37/0045
(Continued)

(56) References Cited

U.S. PATENT DOCUMENTS 4,627,271 A * 12/1986 Abbott .................. G01N 11/08
73/54.06
5,172,585 A    12/1992 Gleissle
(Continued)

FOREIGN PATENT DOCUMENTS

| CN | 101652170 A | 2/2010 |
|---|---|---|
| GB | 2401944 A | 11/2004 |
| NZ | 577687 | 6/2012 |

OTHER PUBLICATIONS

European Patent Office Communication for Application No. 15817374.0-1001 dated Nov. 5, 2019, 9 pages.

*Primary Examiner* — Robert R Raevis
(74) *Attorney, Agent, or Firm* — K&L Gates LLP

(57) ABSTRACT

The present invention relates to a method of continuously determining the shear viscosity (η) of a product paste to be delivered to a spray nozzle for spray-drying applications wherein the continuous determination of the shear viscosity (η) of the product paste is carried out in a bypass to the product paste stream to the spray nozzle.

11 Claims, 3 Drawing Sheets

(58) Field of Classification Search
USPC .................................. 73/54.04–54.09, 54.13
See application file for complete search history.

(56) References Cited

U.S. PATENT DOCUMENTS

| | | | |
|---|---|---|---|
| 5,257,528 A | | 11/1993 | Degouy et al. |
| 5,510,149 A | * | 4/1996 | Schucker .............. B05B 7/2489 |
| | | | 118/666 |
| 6,220,083 B1 | | 4/2001 | Collier |
| 6,280,879 B1 | * | 8/2001 | Andersen ................ H01M 4/04 |
| | | | 29/623.3 |
| 2002/0121129 A1 | | 9/2002 | Baldauf et al. |
| 2009/0107196 A1 | | 4/2009 | Jung |
| 2011/0185795 A1 | | 8/2011 | Colquhoun |
| 2013/0298644 A1 | | 11/2013 | Dean et al. |
| 2014/0005957 A1 | * | 1/2014 | Pihlaja ................... G01N 11/08 |
| | | | 702/50 |
| 2014/0053637 A1 | | 2/2014 | Quillien et al. |
| 2014/0346698 A1 | | 11/2014 | Rijfers et al. |

\* cited by examiner

METHOD OF CONTINUOUSLY MEASURING THE SHEAR VISCOSITY OF A PRODUCT PASTE

CROSS REFERENCE TO RELATED APPLICATIONS

The present application is a National Stage of International Application No. PCT/EP2015/081096, filed on Dec. 22, 2015, which claims priority to European Patent Application No. 14200752.5, filed on Dec. 31, 2014, the entire contents of which are being incorporated herein by reference.

The present invention is directed to a method of continuously measuring the shear viscosity of a liquid product, said shear viscosity being in a range of 20 to 1000 mPa·s and having a shear rate greater than 1000 s$^{-1}$ and a Reynolds number smaller than 2300.

Optimizing the operating conditions of product processing is the object of intensive research in the industry, for example in production lines processing emulsions, suspensions and dispersions in view for example of evaporation or spray-drying processes. Determination of the best economy operating and control of such conditions is important in order to carry out processes in a cheaper and more environmentally sustainable way and to improve the product quality. It is therefore an objective of the present invention to provide methods enabling the skilled person to adapt the processing conditions to the characteristics of the processed product.

The manufacturing of food powders is realized to a great extent by means of spray drying. This process converts emulsions, suspensions and dispersions into powder. Spray nozzles create droplets, which are dried in hot air by evaporating water. The final powder quality, the final powder texture, the dryer process design, the drying efficiency, the walls fouling behaviour, the operational safety, to name only a few characteristics, are directly linked to the spray quality and thus the atomization process.

Known spray drying processes use atomization nozzles with fixed geometries which cannot be adjusted inline to the process and product conditions during start-up, manufacturing operation and shut-down. Instead operators change the nozzle geometries prior to the production cycle without the possibility to cover all the manufacturing situations. Such nozzles are chosen according to water tables. The manufacturing of food powders happens at significantly higher viscosities compared to water. Typical spray viscosities are within in a range comprised between 1 to 300 mPa·s. There is no known nozzle apparatus capable to compete with such a wide range.

As an example, for dairy emulsions at concentrate total solids above 50%, the concentrate viscosity increases in an exponential slope with further increase of total solids. This fact causes problems to spray-drying, if the concentrate viscosity exceeds a design limit of the atomizer nozzles. The design limit is described by means of an atomizer air-core break-down, which stops the creation of droplets and thus stops efficient spray-drying and agglomeration of powders with a required texture. Using prior art spray nozzle apparatus, air-core break downs within atomizer nozzles cannot be determined visually, thus there is currently no means to operate the spray-drying process at its best point without facing issues, such as powder blockages in cones and cyclones, wall fouling or atomizer beard formation, to name just a few issues.

Since the product and process conditions change from start-up to shut-down of the process the quality of the product achieved varies and product build-up can happen on the nozzle itself and on the walls of the spray-drying equipment, in particular on the walls of the drying chamber, in cones of spray-dryers and cyclones, but also in the conveying ducts between the process units.

It is a first objective of the present invention to overcome the problems identified with prior art equipment and methods and to enable to operate a product paste processing, such as for example an evaporator or a spray-drying equipment at its best point and in the most economical way, which involves to be able to process material having the highest possible total solids content and, in the case of spray-drying, to obtain a dry powder having the maximum total solid content possible during atomization, without exceeding the design limit of the atomizers nozzles, which is triggered by the air-core break-down.

It is an object of the present invention to obtain a method of measuring the shear viscosity of a product in line during the production process, such as to enable control of the processing conditions and optimization of the process. In the case of a product to be spray-dried, the spray droplet size of a spray nozzle apparatus is controlled, which allows controlling of the working process and optimization of the spray-drying process. This is particularly useful to achieve a target spray droplet size distribution defined by the Sauter diameter and to keep a target droplet size distribution constant even with changing product or material properties and changing process conditions.

This object is achieved by a method of continuously determining the shear viscosity ($\eta$) of a product paste in a processing line, wherein the continuous determination of the shear viscosity ($\eta$) of the product paste is carried out in a bypass to the product paste stream, wherein the bypass comprises a pump, a flow meter, a differential pressure tube and a pulsation damper and wherein the shear viscosity is in a range of 20 to 1000 mPa·s, the shear rate is greater than 1000 s$^{-1}$ and the Reynolds number is smaller than 2300.

The shear viscosity is used as input parameter to control the process parameters.

In an embodiment, the product is to be processed in a spray-drying equipment or an evaporator. The shear viscosity is used as input parameter to control the evaporator or the spray nozzle. It allows inline control of the evaporator or the spray nozzle. Thus, in the case of a spray nozzle it allows inline control of the spray droplet size, via a stability criterion composed of the spray mass flow rate Qm, the spray pressure P the product density ($\rho$) and the product viscosity ($\eta$). In the case of an evaporator, the liquid film thickness can be maximized without liquid film break-up Furthermore, the control of the spray nozzle thanks to in line determination of the shear viscosity enables to achieve a consistent powder agglomeration in the product during a production cycle independent of the total amount of solid particles (TS) or independent of mass flow rate fluctuations. By this method, a process automation can be achieved through improved and simplified reproducibility and reliability of product properties for different spray-dryer types. A competitive production control is achieved via advanced design of final powder properties like powder moisture, tap density, final agglomerate size and agglomerate stability. Due to the automation the production economy and process efficiency (best-point operation) is also enhanced.

In a preferred embodiment the shear viscosity ($\eta$) of the product paste is determined by the following steps:

a) providing a constant feed-flow-rate of the product paste at laminar flow conditions;

b) determining the mass flow of the product paste;

c) delivering the product paste to a pressure-drop-meter and determining the differential pressure;

d) calculating the shear viscosity (η) of the product paste on the basis of the laminar mass flow and the product density determined in step b), as well as the pressure drop determined in step c).

More preferably, the calculation in step d) considers also the bypass-mass-flow-rate.

This method enables inline recording of product shear viscosities e.g. of coffee and milk products before atomization with its specific product characteristics such as highly viscous (>100 mPa·s) and shear-thinning flow behaviour (determination of $2^{nd}$ Newtonian plateau viscosity (η). The inline shear viscosity information is necessary to operate a controllable evaporator or spray-nozzle inline in order to determine the best point configuration of the evaporator or atomizer and warn in case of design limit achieved. The inline differential pressure drop method allows a calibration of the shear viscosity for Newtonian and in particular Non-Newtonian shear-thinning fluids based on laboratory rheometers.

Other techniques to measure the shear viscosity are either underestimating or overestimating the predefined product shear viscosities of dairy and nutrition products (via laboratory rheometer). In particular for shear-thinning fluids, the frequency-based measuring technique, the Coriolis forced measuring method and the quartz-viscosimetry method do not give the possibility to determine the 2nd Newtonian plateau viscosity of shear-thinning fluids due to the lack of information concerning the applied flow field of the method (and thus unknown shear rates).

Thus, inline recording of the so called second Newtonian plateau viscosity of Non-Newtonian food fluids is possible with the differential pressure drop method and thus allows calibration with predefined product shear viscosity rheograms, which are found from laboratory rheometer measurements.

In the following the invention will be described in further detail by means of an embodiment thereof and the appended drawings.

BRIEF DESCRIPTION OF THE FIGURES

FIG. 1 is a flowchart of a process for controlling the spray droplet size of an agglomeration spray nozzle apparatus. The product paste in FIG. 1 indicated as "concentrate" is delivered to a dosing point 30, which leads a part of the product paste stream into a bypass line 32. The majority of the product paste stream is directed into a main product paste line 34. The bypass line 32 is redirected into the main product paste line 34 at a line junction 36 downstream of a differential pressure drop measuring apparatus 38 provided in the bypass line 32.

Figure 1:
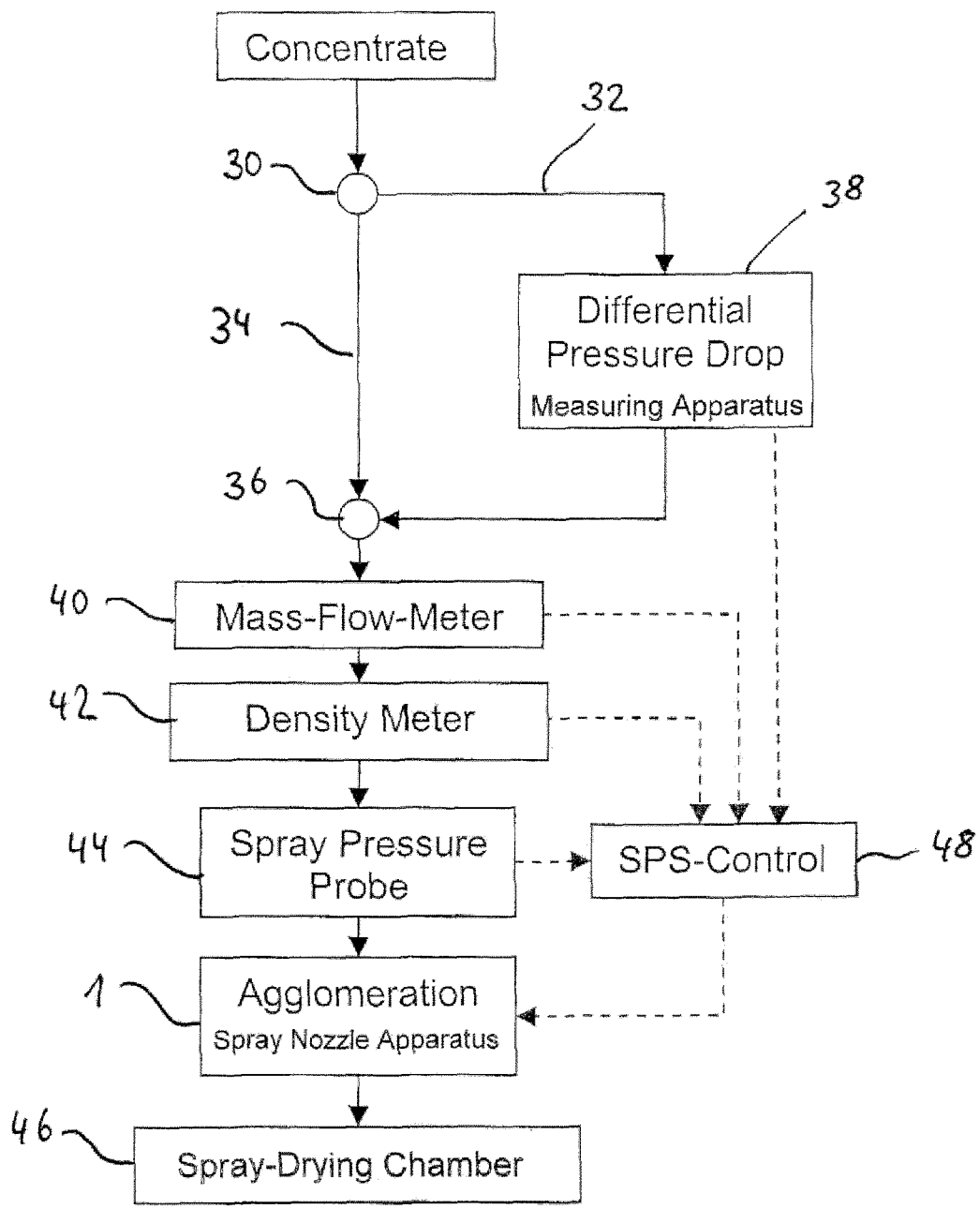
FIG. 1 is a flow chart of a process for controlling the spray droplet size of an spray nozzle apparatus and shows the role of the method of the invention.
Figure 2:
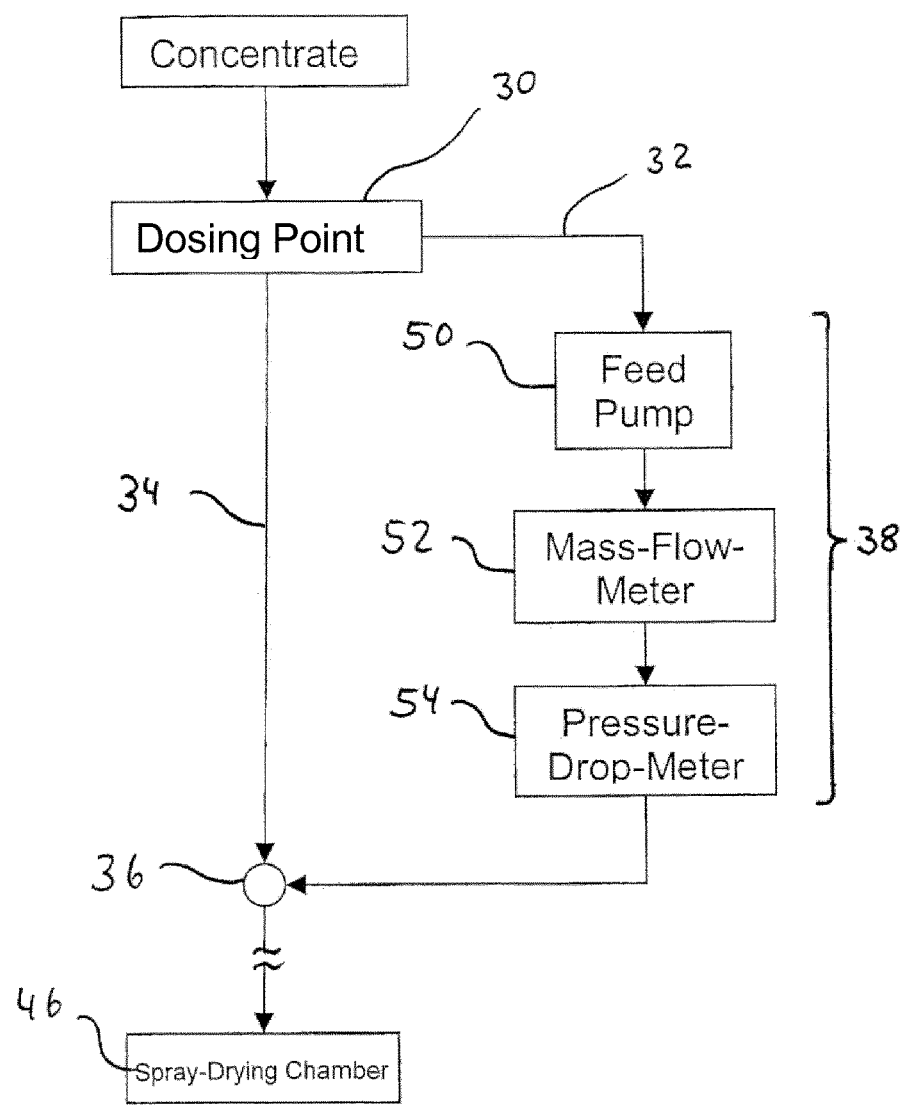
FIG. 2 is a flow chart of a differential pressure drop method according to a specific embodiment of the invention.
Figure 3:
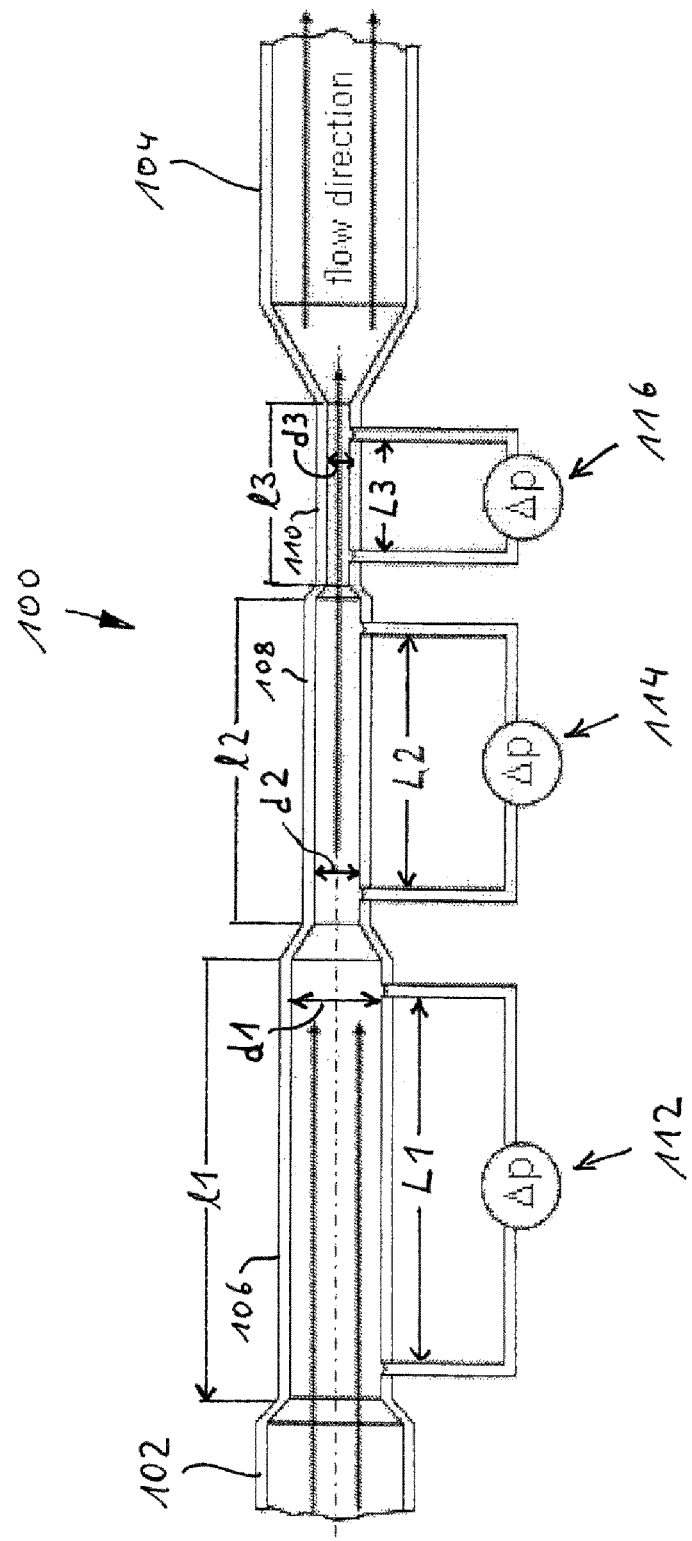
FIG. 3 shows a principle of a measuring apparatus for the differential pressure drop method of the invention In a preferred embodiment, the method of the invention is carried out with a product to be delivered to a spray nozzle. Measuring product input parameters in line with the production process of the powder allows adjusting of the droplet size towards the minimum Sauter diameter possible inline and thus makes it possible to consider the complete range of spray viscosities during the production process of the powder to be produced.

Downstream of the line junction 36 a mass flow meter 40, a density meter 42 and a spray pressure probe 44 are provided in the main product paste line. Downstream of the spray pressure probe 44 the main product paste line 34 enters a spray nozzle apparatus 1 through tube 25. The product paste delivered to the spray nozzle apparatus 1 is then sprayed into a spray drying chamber 46.

The differential pressure drop measuring apparatus 38 determines the shear rate and the shear viscosity η of the product paste delivered to the spray nozzle, according to one preferred embodiment of the invention. The data of the shear rate and shear viscosity η are delivered from the differential pressure drop measuring apparatus 38 to a control device (SPS-control) 48. In the same manner, the product paste mass flow rate $Q_m$ determined in the mass flow meter 40, the product paste density ρ determined in the density meter 42 and the spray pressure P of the product paste determined in the spray pressure probe 44 are also delivered to the control device 48. The shear rate has to be greater than 1000 $s^{-1}$.

Control device 48 comprises a computer which calculates an output control parameter based on the above data delivered to the control device 48 and on the basis of known spray nozzle geometry parameters stored in a memory of the control device 48. The output control parameter is delivered to the spray nozzle apparatus 1 in order to adjust the swirl chamber piston 17 (plunger) to a calculated position in order to obtain a desired swirl chamber volume.

The following equations 1-7 describe the solving procedure how to control the plunger position (given with $h_{sc}$) based on a change in the paste shear viscosity η.

Accordingly the solving procedure is applied for a change in mass flow rate Qm and paste density ρ.

Universal Massflow-Characterization of Pressure Swirl Nozzle Flows:

$$\frac{Qm}{\eta d_{sc}} = 2.1844 \left(\frac{d_{or}}{d_{sc}}\right)^{1.2859} \left(\frac{h_{sc}}{d_{sc}}\right)^{0.4611} \left(\frac{\sqrt{P\rho}\, d_{sc}}{\eta}\right)^{0.9140} \quad (1)$$

The relation between spray pressure P and axial position of the plunger (given with $h_{sc}$) is derived for the example of a shear viscosity change from $\eta_{old}$ to $\eta_{new}$:

$$\frac{\eta_{new}}{\eta_{old}} = \left(\frac{h_{sc,old}}{h_{sc,new}}\right)^{0.4611} \left(\frac{\eta_{new}}{\eta_{old}}\right)^{0.9140} \left(\frac{P_{old}}{P_{new}}\right)^{\frac{0.9140}{2}} \quad (2)$$

Solved for the spray pressure ratio:

$$\frac{P_{old}}{P_{new}} = \left(\frac{\eta_{new}}{\eta_{old}}\right)^{\frac{1-0.9140}{0.4570}} \left(\frac{h_{sc,old}}{h_{sc,new}}\right)^{\frac{-0.4611}{0.4570}} \quad (3)$$

In order to find a direct relation between plunger position $h_{sc}$ and shear viscosity η, the spray pressure ratio has to be found from another equation, see equations 4-6 below:

Universal Spray Droplet Size Characterization of Pressure Swirl Nozzle Sprays:

$$\frac{D_{32,global}}{d_{sc}} = 1.0798\, Re^{-0.2987} We^{-0.1709} \left(\frac{h_{sc}}{d_{sc}}\right)^{-0.0772} \left(\frac{d_{or}}{d_{sc}}\right)^{0.9534} \tag{4}$$

Again, one can derive the Spray Pressure Ratio with the consistency conditions that $D_{32\text{-}global\text{-}old}$ and $D_{32\text{-}global\text{-}new}$ remain constant:

$$\begin{aligned} \frac{D_{32,global,old}}{D_{32,global,new}} &= 1 \\ &= \left(\frac{Re_{old}}{Re_{new}}\right)^{-0.2987} \left(\frac{We_{old}}{We_{new}}\right)^{-0.1709} \left(\frac{h_{sc,old}}{g}\right)^{-0.0772} \\ &= \left(\frac{h_{sc,old}}{h_{sc,new}}\right)^{-0.2987} \left(\frac{\eta_{old}}{\eta_{new}}\right)^{0.2987} \left(\frac{h_{sc,old}}{h_{sc,new}}\right)^{0.2987} \\ &\quad \left(\frac{h_{sc,old}}{h_{sc,new}}\right)^{0.1709\cdot 2} \left(\frac{h_{sc,old}}{h_{sc,new}}\right)^{-0.0772} \end{aligned} \tag{5}$$

And hence the solution, how to control the plunger height $h_{sc,new}$ based on a current position $h_{sc,old}$:

$$\frac{h_{sc,new}}{h_{sc,old}} = \left(\frac{\eta_{new}}{\eta_{old}}\right)^{-1.1289} \tag{6}$$

Combining equations 3 and 6 one receives the solution, how to control the spray pressure:

$$\frac{P_{new}}{P_{old}} = \left(\frac{\eta_{new}}{\eta_{old}}\right)^{0.9508} \tag{7}$$

FIG. 2 is a flowchart of the differential pressure drop method as applied in the differential pressure drop measuring apparatus 38 and according to a preferred embodiment of the invention. A feed pump 50 is provided in the bypass line 32 downstream of dosing point 30. The feed pump 50 ensures a constant feed-flow-rate in the differential pressure drop measuring apparatus 38 to enable shear rates which cover the second Newtonian viscosity plateau. Downstream of the feed pump 50 a mass flow meter 52 is provided through which the product paste in the bypass line 32 is directed into a pressure drop meter 54. The shear viscosity ($\eta$) of the product paste in the bypass line 32 is calculated from the mass flow measured in the mass flow meter 52, the known product density of the product paste and the pressure drop measured in the pressure drop meter 54. This calculation is either made in a computer (not shown) of the differential pressure drop measuring apparatus 38 or, the respective data are delivered to the control device 48 and the shear viscosity $\eta$ is calculated in the computer of the control device 48. In order to consider the fact that the pressure drop is measured in a bypass line 32 the bypass mass flowrate is adjusted by the feed pump 50 until the shear-rate is above $1000\ s^{-1}$, so that the second Newtonian plateau viscosity can be measured by the pressure drop-meter 54 within laminar flow conditions.

A pulsation damper is also preferably provided in the bypass to reduce the noise in the pressure determination.

In the present example the dosing point 30 regulates the bypass flow rate to keep the bypass flow pressure <20 bar at laminar flow conditions, with a Reynolds number below 2300.

FIG. 3 shows the principle of a measuring apparatus (pressure drop meter) for the differential pressure drop method for determination of the second Newtonian plateau viscosity using three independent pressure drop recordings at three different shear-rates.

The pressure drop meter 100 comprises a tube having a fluid inlet section 102 and a fluid outlet section 104 and three pressure drop measuring sections 106, 108, 110 provided between the inlet section 102 and the outlet section 104. The first pressure drop measuring section 106 which is close to the inlet section 102 has a first internal diameter $d_1$ and a first axial length $I_1$. A first differential pressure meter 112 measuring a first pressure drop $\Delta p_1$ is connected to the first pressure drop measuring section 106 in a commonly known matter wherein the axial distance $L_1$ between the two static pressure measuring openings in the wall of the first pressure drop measuring section 106 is substantially equal to the length $I_1$ of the first pressure drop measuring section 106.

The second pressure drop measuring section 108 is provided downstream of the first pressure drop measuring section 106. The internal diameter $d_2$ of the second pressure drop measuring section 108 is smaller than the diameter $d_1$ of the first pressure drop measuring section. The length $I_2$ of the second pressure drop measuring section 108 is shorter than the length of the first pressure drop measuring section 106. The second pressure drop measuring section 108 comprises a second differential pressure meter 114 measuring a second pressure drop $\Delta p_2$ wherein the distance $L_2$ between the two static pressure measuring openings in the wall of the second pressure drop measuring section 108 is shorter than the distance $L_1$ of the first differential pressure meter 112.

A third pressure drop measuring section 110 is provided downstream of the second pressure drop measuring section 108 and the third pressure drop measuring section 110 opens into the outlet section 104. The internal diameter $d_3$ of the third pressure drop measuring section 110 is smaller than the diameter $d_2$ of the second pressure drop measuring section 108 and the length $I_3$ of the third pressure drop measuring section is shorter than the length $I_2$ of the second pressure drop measuring section. The third pressure drop measuring section 110 comprises in a commonly known manner a third differential pressure meter 116 measuring a third pressure drop $\Delta p_3$. The distance $L_3$ between the two static pressure measuring openings in the wall of the third pressure drop measuring section 110 is shorter than the distance $L_2$ of the second differential pressure meter 114.

The differential pressure drop meter 100 allows the measurement of three independent pressure drop recordings of the first, the second and the third differential pressure drop meters. Utilizing these three differential pressure drop probes in series, a single mass flow rate causes three increasing wall shear rates with the decreasing tube diameter.

The following equation 8 is used to calculate the shear viscosity $\eta$ for laminar tube flows (Re<2300), applied to all 3 differential pressures $\Delta p_1$, $\Delta p_2$ and $\Delta p_3$ (respectively measured at 112, 114 and 116, FIG. 8), by replacing $\Delta p_i$ and the corresponding tube dimensions ($R_i$ and $L_i$) in equation 8:

Only, if the shear viscosity $\eta_i$ is equal ($\eta_1 = \eta_2 = \eta_3$) between the 3 differential pressures, the 2nd Newtonian shear viscosity is found and used e.g. in equation 1 and 7, etc.

$$\eta_i = \frac{\pi \cdot R_i^4 \cdot \Delta p_i \cdot \rho}{8 \cdot Qm \cdot L_i} \tag{8}$$

with following definitions of symbols:
$R_i$: tube radius ($R_1$, $R_2$ and $R_3$) in [m]
$\Delta p_i$: tube pressure drop ($\Delta p_1$, $\Delta p_2$ and $\Delta p_3$) in [Pa]
$\rho$: product density in [kg/m3]
Qm: mass flow rate in [kg/s]
$L_i$: tube length (distance $L_1$, $L_2$ and $L_3$) in [m]

TABLE 1

Abbreviations and formula

| Symbol, Abbreviation | Description | Units |
|---|---|---|
| $D_{32,global}$ | Global Sauter diameter as found from PDA measurements of spray | [m] |
| $d_{sc}$ | Swirl chamber diameter (smallest diameter of swirl chamber spiral) | [m] |
| $h_{sc}$ | Swirl chamber height (axial height of swirl chamber) | [m] |
| $d_{or}$ | Orifice diameter (diameter of opening made in orifice plate) | [m] |
| $b_{ch}$ | Width of swirl chamber inlet channel (smallest width of inlet channel which leads into the swirl chamber) | [m] |
| We | Weber number $$We = \frac{\rho_{liquid} u_{bulk}^2 d_{orifice}}{\sigma_{liquid}}$$ | — |
| Eu | Euler number $$Eu = \frac{P}{\rho_{liquid} u_{bulk}^2}$$ | — |
| Re | Reynolds number $$Re = \frac{\rho_{liquid} u_{bulk} h_{sc}}{\mu}$$ | — |
| $u_{bulk}$ | Bulk velocity at swirl chamber inlet $$u_{bulk} = \frac{Qm}{\rho_{liquid} h_{sc} b_{ch}}$$ | [m/s] |
| Qm | Mass flow rate | [kg/s] |
| P | Spray pressure | [Pa] |
| $\rho_{liquid}$ | Liquid density | [kg/m$^3$] |
| $\eta_{liquid}$ | Liquid shear viscosity | [Pa · s] |
| $\sigma_{liquid}$ | Surface tension | [N/m] |
| PDA | Phase-Doppler Anemometry | — |

The invention should not be regarded as being limited to the embodiment shown and described in the above but various modifications and combinations of features may be carried out without departing from the scope of the following claims.

The invention claimed is:

1. A method of continuously determining a shear viscosity of a product paste in a processing line, the method comprising:
   continuously determining the shear viscosity of the product paste in a bypass to a stream of the product paste, the bypass comprising a pump, a flow meter, a differential pressure tube and a pulsation damper, and the shear viscosity is in a range of 20 to 1000 mPa·s, the shear rate is greater than 1000 s$^{-1}$, and the Reynolds number is less than 2300;
   delivering the product paste to a spray nozzle for a spray-drying application; and
   adjusting a droplet size of the product paste, the adjusting comprises a control device calculating an output control parameter based on the shear rate and the shear viscosity of the product paste and also based on spray nozzle geometry parameters stored in a memory of the control device, the output control parameter is delivered to the spray nozzle which adjusts a swirl chamber piston to a calculated position to obtain a desired swirl chamber volume.

2. The method according to claim 1, wherein the determining the shear viscosity of the product paste comprising:
   a) providing a constant feed-flow-rate of the product paste;
   b) determining a mass flow of the product paste;
   c) delivering the product paste to a pressure-drop-meter and determining a pressure drop;
   d) calculating the shear viscosity of the product paste on the basis of the mass flow determined in step b), a known product density, as well as the pressure drop determined in step c).

3. The method according to claim 2, wherein the calculation in step d) considers also the constant bypass-mass-flow-rate.

4. The method according to claim 2, wherein the determination of the pressure drop in step c) is carried out according to a differential pressure drop method.

5. The method according to claim 2, wherein the pressure drop meter comprises a tube having a fluid inlet section and a fluid outlet section and a first, second, and third pressure drop measuring sections provided between the inlet section and the outlet section.

6. The method according to claim 5, wherein the second pressure drop measuring section is provided downstream of the first pressure drop measuring section, has a second internal diameter of the second pressure drop measuring section smaller than the first internal diameter of the first pressure drop measuring section, and has a second axial length shorter than the first axial length of the first pressure drop measuring section.

7. The method according to claim 6, wherein the second pressure drop measuring section comprises a second differential pressure meter measuring a second pressure drop, a second axial distance between second two static pressure measuring openings in a second wall of the second pressure drop measuring section is shorter than the first axial distance of the first differential pressure meter.

8. The method according to claim 5, wherein the third pressure drop measuring section is provided downstream of the second pressure drop measuring section opens into the outlet section, and the third pressure drop measuring section has a third internal diameter smaller than the second internal diameter of the second pressure drop measuring section and has a third axial length shorter than the second axial length of the second pressure drop measuring section.

9. The method according to claim 8, wherein the third pressure drop measuring section comprises a third differential pressure meter measuring a third pressure drop, and a third axial distance between third two static pressure measuring openings in a third wall of the third pressure drop measuring section is shorter than the second axial distance of the second differential pressure meter.

10. The method according to claim 5, wherein the first pressure drop measuring section is close to the inlet section, has a first internal diameter and a first axial length, and is connected to a first differential pressure meter measuring a first pressure drop.

11. The method according to claim 10, wherein a first axial distance between first two static pressure measuring openings in a first wall of the first pressure drop measuring section is substantially equal to the first axial length of the first pressure drop measuring section.

* * * * *